US00PP11013P

United States Patent [19]

Evison et al.

[11] Patent Number: Plant 11,013

[45] Date of Patent: Jul. 27, 1999

[54] CLEMATIS VARIETY NAMED 'EVISIX'

[75] Inventors: Raymond J. Evison, Channel Islands, United Kingdom; Mogens N. Olesen, Fredensborg, Denmark

[73] Assignee: Poulsen Roser International, SARL, Souvans, France

[21] Appl. No.: 08/926,834

[22] Filed: Sep. 10, 1997

[51] Int. Cl.[6] ..... A01H 5/00

[52] U.S. Cl. ..... Plt./54.1

[58] Field of Search ..... Plt./54.1

*Primary Examiner*—Elizabeth Kemmerer

[57] ABSTRACT

A new compact growing Clematis cultivar which produces violet blue flowers with contrasting yellow anthers over a long flowering season from summer through fall. The cultivar is compact and upright in growth, of a non-clinging character with distinct bronzed-green foliage. The variety successfully propagates from softwood cuttings and is suitable for ornamental use in outdoor settings in a variety of climatic conditions. This new and distinct variety has shown to be uniform and stable in the resulting generations from propagation.

2 Drawing Sheets

SUMMARY OF THE INVENTION

The present invention constitutes a new and distinct variety of Clematis which originated as a seedling of a crossing of Daniel Deronda and an unnamed parent in 1988 at Domarie Vineyards. The two parents were crossed and the resulting seed was planted in a controlled environment. The new variety is named 'EVIsix'.

The objective of the hybridization of this Clematis variety for commercial glasshouse and nursery culture was to create a new and distinct variety with:

1. Attractive and unusual flowers and tepals;
2. Violet blue tepals;
3. Yellow anthers and violet blue filaments;
4. Attractive foliage;
5. Long flowering season;
6. Compact, non-clinging growth.

These qualities required improvement in Clematis varieties that were in commercial cultivation and the objectives have been substantially achieved in the new variety, as evidenced by the unique combination of characteristics that are present in 'EVIsix' which distinguish it from all other varieties of which we are aware.

The seed from the hybridization was germinated and evaluations were conducted on the resulting Clematis plant in a controlled environment.

'EVIsix' was selected by Raymond J. Evison and Mogens N. Olesen in their Clematis development program in Domarie Vineries Les Sauvagees, St. Sampsons, Guernsey, Channel Islands, United Kingdom in 1988.

Asexual reproduction of 'EVIsix' by cuttings was first done by Raymond J. Evison and Mogens N. Olesen in Domarie Vineries Les Sauvagees, St. Sampsons, Guernsey, Channel Islands, United Kingdom in 1988. This initial and subsequent propagations have demonstrated that the characteristics of 'EVIsix' are true to type and are transmitted from one generation to the next.

BRIEF DESCRIPTION OF THE DRAWING

The accompanying color illustrations show as true as is reasonably possible to obtain in color photographs of this type, the typical characteristics of the buds, tepals and leaves of the new variety, with different tepals shown in various stages of maturity. The tepal form, tepal counts, tepal colors, tepal buds, tepal parts, pedicels and the cultivar's foliage are depicted.

DETAILED DESCRIPTION OF THE VARIETY

The following is a detailed description of 'EVIsix', as observed in its growth throughout the flowering period in glasshouses at Domarie Vineries Les Sauvagees, St. Sampsons, Guernsey, Channel Islands, United Kingdom. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing CLematis variety is x. Eriostemon. Chart 1 details several physical characteristics of the applicant and the comparision varieties.

Chart 1

| | 'EVIsix' | 'Eriostemon' |
|---|---|---|
| Plant Height | <1 meter | 1–3 meters |
| Shoot Anthocyanin | strong | medium |
| Flowering Period | summer/fall | summer fall |
| Anther Color | Yellow | Cream/white |
| Tepal Color (upper) | RHS 90 B Violet Blue | Blue |
| Plant Habit | Climbing/ non-clinging | Climbing/ non-clinging |

Parents: Daniel Deronda x Unknown seedling.
Classification:
*Botanical.*—*Clematis l.*
*Commercial.*—Late flowered form.

Flower and Flower Bud

Blooming habit: Summer and Fall.
Flower bud:
*Size.*—20–30 mm in length.
*Bud form.*—Ovoid.
*Bud color.*—Purple bud at ¼ opening.
*Sepals.*—None.
*Peduncle.*—Surface: Smooth. Length: 130–180 mm average length. Color: Dark red. Orientation: Horizontal.
*Receptacle.*—Size: Small. Color: Red-green.

*Borne.*—In clusters and singly. Shape: Compound cymes.

Flower bloom:

*Size.*—Small, 80 mm. on average.

*Form.*—Upon opening, campanulate with tepals reflexing.

*Color.*—Upon opening, the upper surface is R.H.S. 90 B of the Violet Blue Color Group. Upon opening, the reverse side is R.H.S. 90 C of the Violet Blue Color Group. After opening, the upper surface is R.H.S. 90 B the Violet Blue Color Group. After opening, the reverse surface is R.H.S. 90 B of the Violet Blue Color Group. The base of the tepals is R.H.S. 90 A of the Blue Group. The general tonality from a distance is Purple.

*Variations.*—Uniform.

*Fragrance.*—None.

*Lasting quality on plant and as a cut flower.*—Long lasting.

Tepals:

*Petalage.*—Single. Average range: 4–6.

*Shape.*–Individual tepal shape is elliptic.

*Cross section.*—Reflexed.

*Undulation of margin.*—Moderately undulated.

*Tepal apex.*—Narrowly acute.

*Recurvature of tip.*—Recurved.

*Persistence.*—Drop off cleanly.

*Arrangement.*—Tepals are arranged regularly.

Reproductive organs:

*Pollen.*—Color: Cream. Abundance: Little.

*Anthers.*—Size: Medium. Color: Yellow. Arrangment: Regular.

*Filaments.*—Color: Purple.

*Stigmas.*—Central, hidden until anthers open out. Feathery in appearance.

Plant

Plant form: Upright.

Plant growth: Average vigor.

Height: Season's growth attains 0.75–1 meter.

Hardiness: Trials to date show the variety hardy in USDA Zones 4–9.

Stems:

*Color.*—Young wood: Green. Older wood: Brown.

*Internodes.*—Cylindrical. Length 100 mm.

*Petioles.*—Incidence: Few. Size: Average length: 20 mm. Color: Dark Red. Clasping: None.

Bark:

*Young wood.*—Hairy.

*Older wood.*—Smooth.

Plant foliage: Deciduous. Simple.

*Leaf size.*—Medium. 90 mm in length and 30 mm in width.

*Abundance.*—Limited.

*Color.*—Top: Dark green. R.H.S. 137 A of the Green Color Group. Bottom: Medium green. R.H.S. 137 C of the Green Color Group. New growth: Light green, occasional bronze coloration. Older growth: Dark green. R.H.S. 137 A of the Green Color Group.

Plant leaves and leaflets:

*Stipules.*—Absent.

*Petiole.*—Length: 20 mm. Underneath: Without prickles.

*Leaf edge.*—Terminal leaflet margin is entire.

*Shape.*—Base of leaflet: Rounded. Apex of leaflet: Acute.

*Texture.*—Thick. Upper side: Rough. Lower side: Ribbed.

*Surface.*—Matte Finish.

Disease resistance: Subject to any disease that normally attacks the species, however the variety is more tolerant to Clematis Wilt than some Clematis.

We claim:

1. A new and distinct cultivar of Clematis plant, substantially as herein shown and detailed, as a distinct and novel clematis cultivar due to its abundant violet-blue flowers with contrasting yellow anthers, bronzed green foliage and compact habit make this a unique cultivar suitable for use in a variety of garden uses and a variety of clematis conditions.

* * * * *

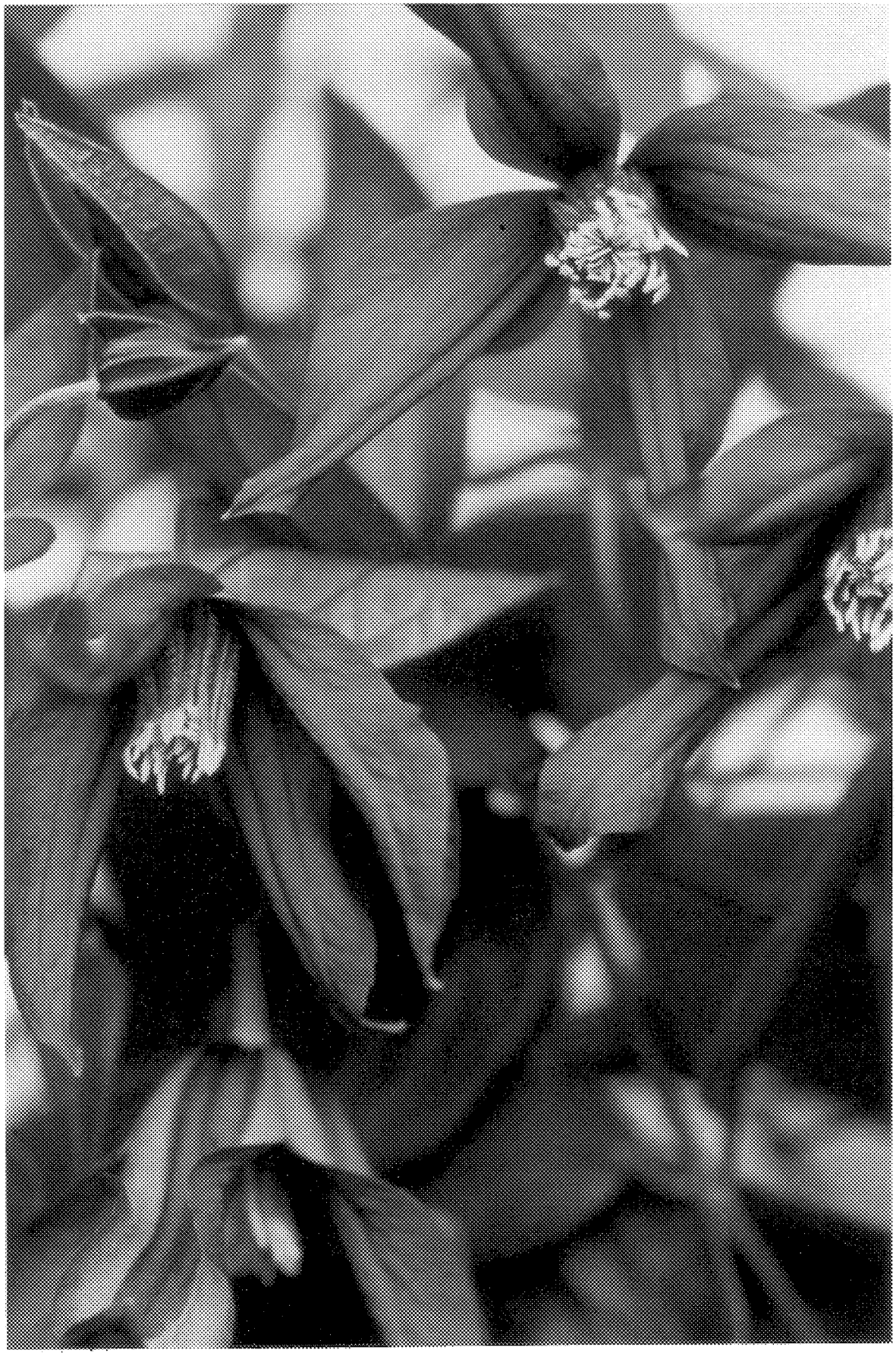

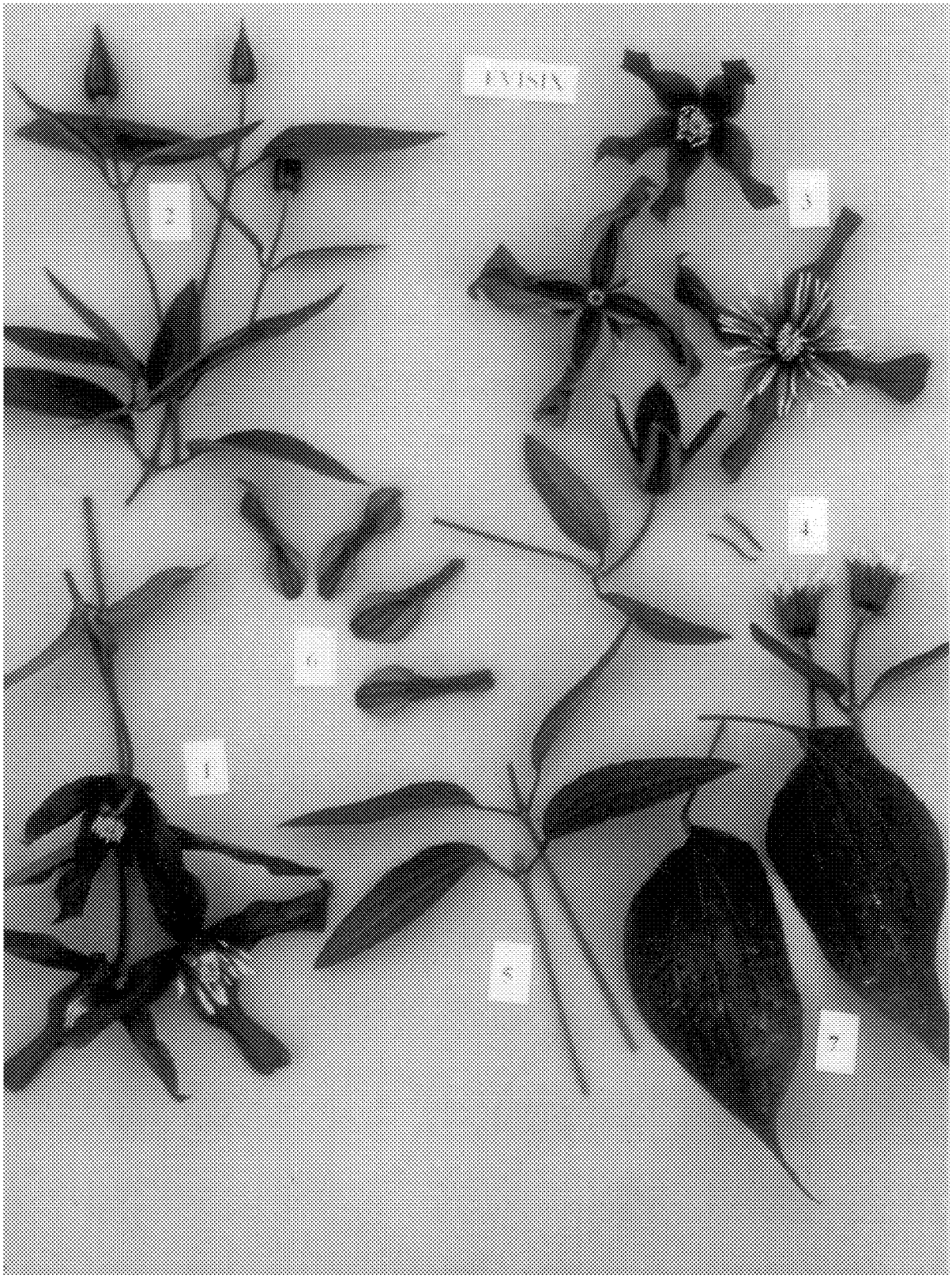
1
2
3
4
5
6
7